United States Patent
Kalweit et al.

Patent Number: 6,005,084
Date of Patent: Dec. 21, 1999

[54] ASYMMETRIC TRIPHENYLENEDIOXAZINE COMPOUNDS

[75] Inventors: Detlef Kalweit, Basel, Switzerland; Roland Wald, Huningue, France

[73] Assignee: Clariant Finance (BVI) Limited, Tortola, Virgin Islands (Br.)

[21] Appl. No.: 08/698,533

[22] Filed: Aug. 15, 1996

[51] Int. Cl.⁶ ............................ C09B 62/02; C09B 62/20
[52] U.S. Cl. ............................ 534/632; 534/637; 544/76
[58] Field of Search ............................ 8/657, 658, 94.18, 8/190, 115.61, 918, 924; 544/76, 326, 330; 534/637, 632

[56] References Cited

U.S. PATENT DOCUMENTS

| | | | |
|---|---|---|---|
| 4,935,501 | 6/1990 | Tzikas et al. | 534/634 |
| 5,227,477 | 7/1993 | Auerbach et al. | 534/634 |
| 5,270,454 | 12/1993 | Hoppe et al. | 534/634 |
| 5,274,083 | 12/1993 | Herd et al. | 534/618 |
| 5,340,928 | 8/1994 | Hoppe et al. | 534/618 |
| 5,420,256 | 5/1995 | Eizenhofer et al. | 534/618 |

Primary Examiner—Mukund J. Shah
Assistant Examiner—Deepak R. Rao
Attorney, Agent, or Firm—Gabriel Lopez

[57] ABSTRACT

Fibre-reactive asymmetrical triphenodioxazine compounds conform to the formula I

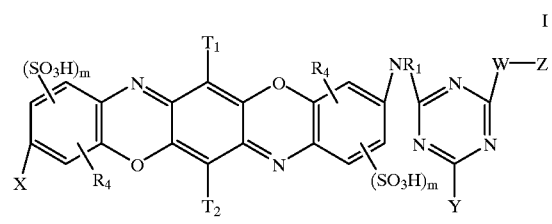

where the individual symbols are as defined in the description, and mixtures thereof and are present in the form of a free acid or as salt. They are used as reactive dyes for dyeing or printing hydroxyl-containing or nitrogenuos organic substrates, such as leather or fiber material consisting of or comprising natural or synthetic polyamides or natural or regenerated cellulose; the most preferred substrate is textile material consisting of or comprising cotton.

1 Claim, No Drawings

ASYMMETRIC TRIPHENYLENEDIOXAZINE COMPOUNDS

This invention is concerned with asymmetric triphenodioxazine compounds containing fibre-reactive groups, processes for preparing the same and their use as fibre-reactive dyes in dyeing or printing processes.

The invention provides in one of its aspects a compound according to the formula (I)

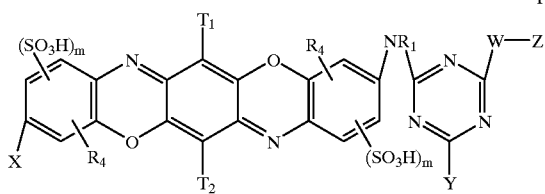

or its salts or mixtures thereof,
wherein
$T_1$ and $T_2$ are independently of each other hydrogen, chlorine, bromine, $C_{1-4}$ alkyl, $C_{1-4}$ alkoxy or phenoxy,
X is -$NR_2R_3$ or $NR_1$-Z,
each $R_1$ is independently of the other hydrogen, $C_{1-4}$ alkyl, or substituted $C_{1-4}$ alkyl,
$R_2$ and $R_3$ are independently of each other hydrogen, $C_{1-4}$ alkyl, substituted $C_{1-4}$ alkyl or cyclohexyl, or
-$NR_2R_3$ is a 5- or 6-membered heterocyclic ring which may include one or two additional hetero atoms selected from oxygen, nitrogen or sulphur atoms and which is optionally further substituted with, for example groups selected from amino, sulpho, hydroxyl, alkyl, alkoxy or halogen, e.g. F, Cl or Br,
$R_4$ is hydrogen, halogen, $C_{1-4}$ alkyl, $C_{1-4}$ alkoxy or carboxyl,
W is an aliphatic, araliphatic, aromatic, or cycloaliphatic diamino bridge member,
Y is fluorine, chlorine or $C_{1-4}$ alkoxy, and
each Z is independently of the other a heterocyclic fibre-reactive radical containing at least one labile fluorine or chlorine atom, and
each m is independently of the other 1 or 2.

Unless otherwise stated, each alkyl or alkylene group in the present description can be linear or branched. In a hydroxyl-substituted alkyl or alkylene group attached to a nitrogen atom, the hydroxyl group is preferably attached to a carbon atom which is not directly bonded to a nitrogen atom. Each alkyl group can be methyl, ethyl, propyl or butyl; propyl or butyl groups may be linear or branched. Each alkoxy group may be methoxy, ethoxy, propoxy or butoxy; propoxy or butoxy groups may be linear or branched.

When a halogen is employed as a substituent on an alkyl or phenyl group it may be a fluorine, chlorine or bromine atom, preferably chlorine.

$T_1$ and $T_2$ are preferably chlorine.

When $R_1$ is a substituted alkyl group, it is preferably mono-substituted by hydroxyl, chlorine or cyano, preferably hydroxyl or chlorine.

Each $R_1$ is preferably $R_{1a}$, wherein each $R_{1a}$ is independently of the other, hydrogen, methyl, ethyl, or 2-hydroxyethyl. More preferably $R_1$ is $R_{1b}$, wherein each $R_{1b}$ independently of the other is hydrogen or methyl. In a particularly preferred embodiment, each $R_1$ is hydrogen.

When $R_2$ and $R_3$ independently of each other are substituted alkyl groups, they are preferably mono-substituted with hydroxyl, halogen, cyano, sulpho, sulphato, or carboxyl, more preferably hydroxyl, sulpho or sulphato.

$R_2$ and $R_3$ independently of each other are preferably $R_{2a}$ and $R_{3a}$ wherein $R_{2a}$ and $R_{3a}$ are independently selected from hydrogen, methyl, ethyl, 2-hydroxyethyl, 2-sulphoethyl or 2-sulphatoethyl, or -$NR_{2a}R_{3a}$ is pyrrolidine, piperidine, or morpholine or is

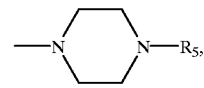

wherein $R_5$ is hydrogen, methyl, ethyl, 2-hydroxyethyl, or 2-aminoethyl.

More preferably $R_2$ is $R_{2b}$ wherein $R_{2b}$ is hydrogen, methyl, ethyl or 2-hydroxyethyl. Particularly preferably $R_2$ and $R_3$ are each hydrogen.

$R_4$ is preferably $R_{4a}$ wherein $R_{4a}$ is hydrogen, methyl, methoxy or carboxyl; in particular $R_4$ is hydrogen.

Y is preferably Y' wherein Y' is fluorine, chlorine or methoxy, preferably Y is Y" wherein Y" is fluorine or chlorine.

When W is an aliphatic diamino bridge it is preferably derived from a $C_{2-6}$ alkylenediamine which may be unsubstituted or substituted, in which case hydroxyl is a preferred substituent.

When W is an araliphatic diamino bridge it is preferably derived from a $C_{1-4}$ alkylenephenylenediamine whose phenylene radical is unsubstituted or carries 1 or 2 substituents selected from the group consisting of $C_{1-4}$ alkyl, $C_{1-4}$ alkoxy, halogen, hydroxyl, sulpho and carboxyl.

When W is an aromatic diamino bridge it is preferably derived from phenylenediamine or from Q-linked diphenylenediamine (in which case Q is a direct bond or a divalent bridge member selected from, for example -CH=CH-, -CH$_2$CH$_2$-, -NH-, -NHCO- or -NHCONH-) whose phenylene radicals are unsubstituted or carry 1 or 2 substituents selected from the group consisting of $C_{1-4}$ alkyl, $C_{1-4}$ alkoxy, halogen, hydroxyl, sulpho and carboxyl.

When W is a cycloaliphatic diamino bridge it is preferably derived from unsubstituted or substituted piperazine. As substituents, one can mention $C_{1-4}$ alkyl, $C_{1-4}$ alkoxy, halogen, e.g., fluorine or chlorine, hydroxyl, sulpho and carboxyl.

W is preferably W' wherein W' is -$NR_{1a}$-$B_1$-$NR_{1a}$-,

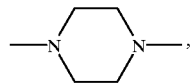

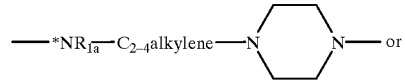

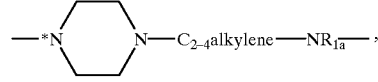

wherein the marked nitrogen atom is bonded to a carbon atom of the triazine ring, and $B_1$ is $C_{2-6}$ alkylene, $C_{3-6}$ hydroxyalkylene, phenylene, an aryl group containing at least one, e.g. 1 or 2, sulpho substituent or an araliphatic group containing said sulpho-substituted aryl group, preferably

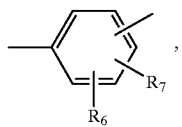

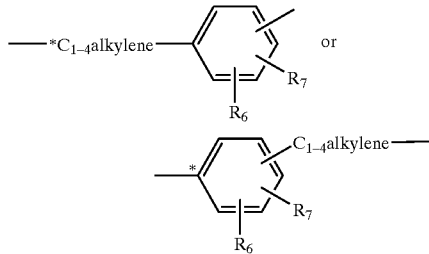

wherein the marked carbon atom is bonded to the -NR$_{1a}$- group which is linked to the carbon atom of the triazine ring, R$_6$ and R$_7$ are each independently of the other hydrogen, halogen, hydroxyl, C$_{1-4}$ alkyl, C$_{1-4}$ alkoxy, carboxyl or sulpho.

R$_6$ is preferably R$_{6a}$ wherein R$_{6a}$ is hydrogen, hydroxyl, chlorine, methyl, methoxy, carboxyl or sulpho.

R$_7$ is preferably R$_{7a}$ wherein R$_{7a}$ is hydrogen, methyl, methoxy or sulpho.

B$_1$ is preferably B$_{1a}$ wherein B$_{1a}$ is C$_{2-3}$ alkylene, C$_{3-4}$ hydroxyalkylene or

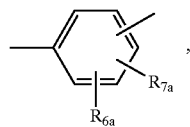

wherein the unspecified bonds are arranged meta or para; particularly preferably B$_1$ is B$_{1b}$ wherein B$_{1b}$ is

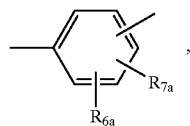

wherein the unspecified bonds are arranged meta or para.

When W is an aliphatic bridging member it is preferably is -NR$_{1b}$-B$_{1a}$-NR$_{1b}$,

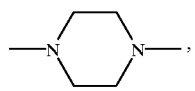

wherein B$_{1a}$ has its aliphatic significances;

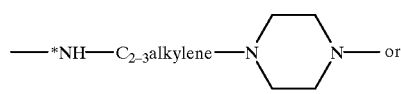

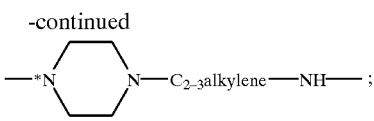

The most preferred group W is W''' wherein W''' is -NR$_{1b}$-B$_{1b}$-NR$_{1b}$-.

The reactive radical Z is preferably Z' wherein Z' is a monofluoropyrimidinyl radical of the formula

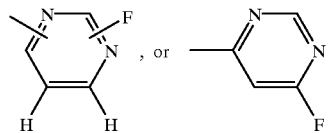

or a radical of the formula (a)

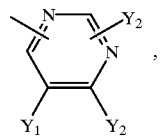

(a)

where Y$_1$ is hydrogen, chlorine or cyano and the two groups Y$_2$ are identical and each Y$_2$ is fluorine or chlorine.

Z is more preferably Z'' wherein Z'' is a radical of the formula

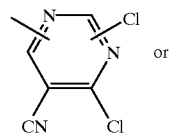

(a$_1$)

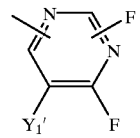

(a$_2$)

where Y$_1$' is hydrogen or chlorine.

X is preferably X' wherein X' is -NR$_{2a}$R$_{3a}$ or -NR$_{1a}$-Z'; more preferably X'' wherein X'' is -NHR$_{2b}$ or -NR$_{1b}$-Z'' most preferably X is -NH$_2$.

m is preferably 1 in which case the sulpho group is preferably in one of the ortho positions relative to X or relative to -NR$_1$-triazinyl.

In a preferred aspect of the invention there is provided a compound of the formula Ia

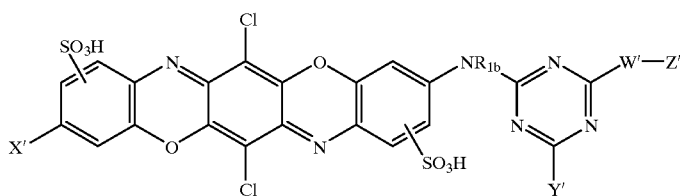

Ia its salts or mixtures thereof,
wherein X', Y", W', Z' and $R_{1b}$ are as defined above.

In a more preferred compound of the formula Ia:
(1) $R_{1b}$ is hydrogen;
(2) W' is W";
(3) those of (1) or (2) where Z' is Z";
(4) those of (3) where X' is X";
(5) those of (2) where W' is W'";
(6) those of (5), where X' is $-NH_2$.

The nature of the cation of the sulpho groups and of any carboxyl groups additionally present in compounds of the formula I when they are in salt form is not a critical factor; it can be any desired non-chromophoric cation customary in the chemistry of reactive dyes. The essential requirement is that the corresponding salts meet the condition of solubility in water.

Examples of suitable cations are alkali metal ions, for example lithium, sodium or potassium or unsubstituted or substituted ammonium ions, for example ammonium, mono-, di-, tri- and tetramethylammonium, triethylammonium and mono-, di- and triethanolammonium.

Preferred cations are the alkali metal ions and ammonium, of which sodium and/or lithium is particularly preferred.

In general, in any one compound of the formula I, the cations of the sulpho groups and any carboxyl groups can be identical or different and constitute a mixture of the above-mentioned cations; that is, the compound can also be present in mixed salt form.

The invention provides in another of its aspects a process for preparing compounds of the formula I its salts or mixtures thereof, characterized in that 1 mole of a compound of the formula IIa

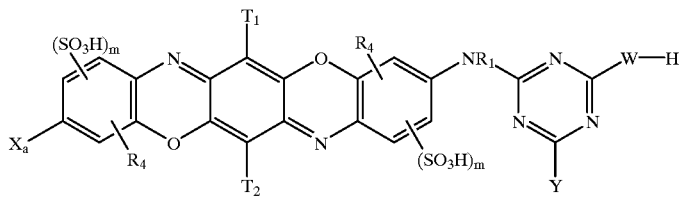

IIa or a salt thereof is reacted with at least 1 or at least 2 moles of the compound Z-Hal,
where Z is as defined above and Hal is fluorine or chlorine, wherein $X_a$ is $-NR_2R_3$ or $-NR_1-H$ and the other variables are as defined above.

A compound of the formula I where X is $-NR_2R_3$ can also be obtained by a process in which 1 mol of a compound of the formula IIb or a salt thereof

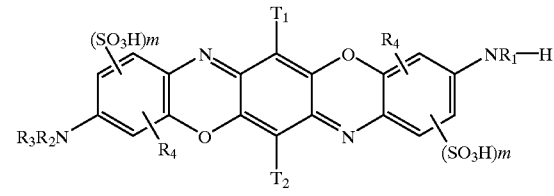

is reacted with 1 mole of a compound of the formula III

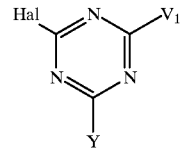

III where Hal is fluorine or chlorine and $V_1$ is fluorine, chlorine or -W-Z, and Y, W and Z $R_1$ to $R_4$, $T_1$, $T_2$ and m are each as defined above. If $V_1$ is fluorine or chlorine, the product is subsequently condensed with a compound of the formula H-W-Z.

The above-mentioned condensation reactions are preferably carried out in a medium having a weakly acidic to weakly alkaline pH. The temperature of the reaction of an amine with a halogen compound is dependent on the structure of the halogen compound, for example, temperatures of 50–80° C. are used for replacing the second chlorine atom of the triazine and temperatures of 0–20° C. are used for the reaction with a halopyrimidine.

The compounds of the formula I can be isolated in a conventional manner, for example the compounds can be salted out of the reaction mixture using alkali metal salts, filtered off and dried at slightly elevated temperature under reduced pressure.

Depending on the reaction and isolation conditions, a compound of the formula I is obtained as a free acid or preferably in salt form or as a mixed salt which contains, for example one or more of the above-mentioned cations.

However, salts or mixed salts can also be prepared in a conventional manner starting from the free acid, and vice versa.

When reacting with a fluorine- and/or chlorine-containing pyrimidine compound Z-Hal, the linking of Z with the bridge member W and/or the $NR_1$ radical, is not fixed, that is positional isomers are possible as regards the fluorine or chlorine substitution on the ring(s). Positional isomers are also possible because of the variable substitution in the triphendioxazine ring skeleton. The compounds of the formula I are therefore obtained as a mixture of positional isomers depending on the position of the radical Z and also in respect of the substitution in the ring skeleton. Separation into the individual isomers can in principle be effected by conventional methods, but is generally not necessary.

The starting compounds of the formula IIa are obtained by reacting a compound of the formula IV with the diamine of the formula H-W-H in a conventional manner,

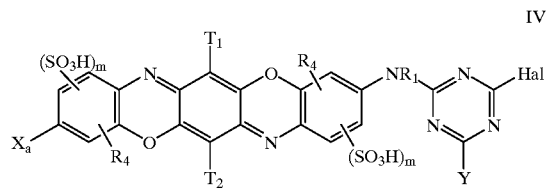

wherein the substituents are as defined above.

The starting compounds of the formulae IIb, III and IV are either known or can be prepared in a known manner.

customary for reactive dyes. Dyeing is preferably carried out by the exhaust process from an aqueous medium and within the temperature range of 30–100° C., in particular at 50–60° C. or 80–100° C. Preference is given to a liquor ratio (liquor to substrate) of 6:1 to 30:1, or preferably of 10:1 to 20:1.

The compounds of formula I give good exhaustion and fixation values. The unfixed dye portion is readily washed off. The dyeings and prints obtained have good light fastness. They additionally have good wet fastness properties for example in respect of wash, water, seawater and perspiration fastness and have good resistance to oxidative effects and also to chlorine-containing water, hypochlorite bleach, peroxide bleach and also to perborate-containing detergents. Dyeings are produced in blue shades.

In addition to their use as the sole dye in dyeing or printing processes and in view of the surprising discovery that the compounds of the formula (I) or salts thereof can be employed in low-salt dyebaths with good solubilities therein, the compounds of formula (I) or salts thereof can be employed in dyeing processes as a mixture together with certain yellow and red dyestuffs having comparable dyeing characteristics, e.g. general fastness properties and exhaustion values and solubility in low-salt dyebaths. The dyeings obtained give exhaustion and fixation values comparable to those described in the preceding paragraph for the sole dye.

Particularly preferable dyeings from the above-mentioned mixtures of dyes are obtained when compounds of the formula (I) are combined with a yellow dyestuff of formula (V),

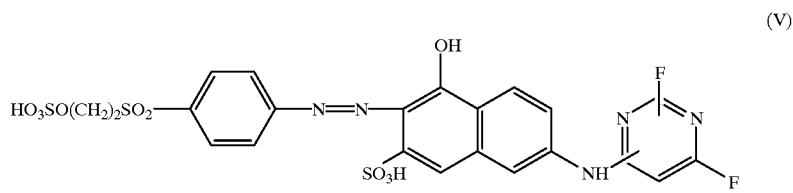

and a red dyestuff of formula (VI)

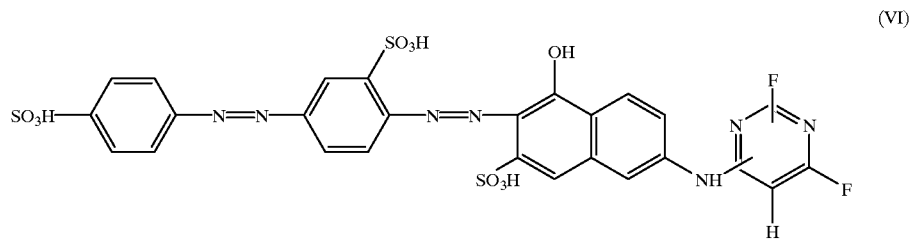

The compounds of the formula I and mixtures thereof are reactive dyes; they are suitable for dyeing or printing hydroxyl-containing or nitrogen-containing organic substrates. Preferred substrates are leather and fibre materials consisting of or comprising natural or synthetic polyamides and in particular natural or regenerated cellulose, such as cotton, filament viscose or staple viscose. The most preferred substrate is textile material consisting of or comprising cotton.

The compounds of the formula I or its salts or mixtures thereof can be used as the sole dye in dyeing liquors or in print pastes according to all dyeing or printing processes The component dyestuffs can be combined in any desired proportions in order to obtain desirable shades of dyeing.

Accordingly, in another aspect of the invention there is provided a dyeing composition comprising (A) a compound of the formula (I), (B) a compound of formula (V) and (C) a compound of the formula (VI), or their salts.

Dyeing using a mixture of the afore-mentioned compounds may be carried out using the exhaust process from an aqueous medium at a temperature of between 40 to 80° C., more preferably 50 to 60° C. and at a salt, e.g. Glauber's salt, concentration of from 0 to 80 g/l, preferably 0 to 50 g/l, more preferably 5 to 20 g/l and most preferably 5 to 10 g/l. The liquor ratio is preferably 6:1 to 30:1, more preferably 10:1 to 20:1.

Dyeings obtained from dyebaths comprising a mixture of the compounds of formula (I), (V) and (VI) (so-called trichromatic dyebaths) are of bluish-brown to reddish-brown shades depending on the relative proportions of the component compounds (I), (V) and (VI) in the mixture.

The examples which follow illustrate the invention. Unless otherwise stated, parts and percentages are by weight; the temperatures are reported in degrees Celsius.

EXAMPLE 1

140 parts of the triphendioxazine compound of the formula 1a

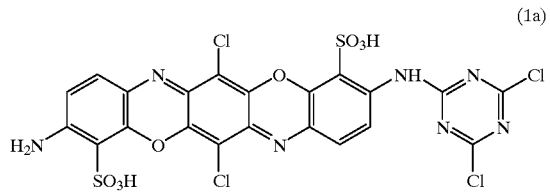

(1a)

prepared as described in Example 1 of DE-A40 05 551, are provided in 1800 parts of water. Lithium hydroxide is added to adjust the pH of the solution to 5–6. 75 parts of the condensation product of the formula 1b, which is prepared at pH 5–6 from 56 parts of 2,4-diaminobenzenesulphonic acid and 33 parts of 2,4,6-trifluoropyrimidine, are added.

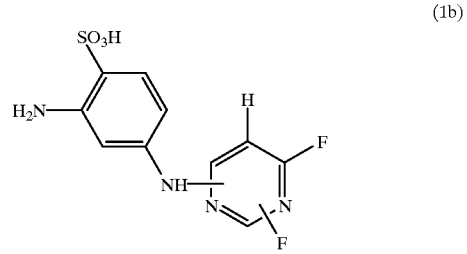

(1b)

During the condensation reaction, which is carried out at temperatures between 60–70°, the pH is maintained at 5–6 by appropriate additions of lithium hydroxide. After the reaction has ended, the dye formed is salted out with sodium chloride, filtered off and dried at 50° under reduced pressure. The dye (in the form of the free acid) has the formula 1c The same dye is obtained by dissolving 60 parts of the condensation product of the formula 1b in 600 parts of water and reacting at 0–5° with 40 parts of cyanuric chloride while the pH is maintained at 5–6 with lithium hydroxide. The resulting intermediate of the formula 1d

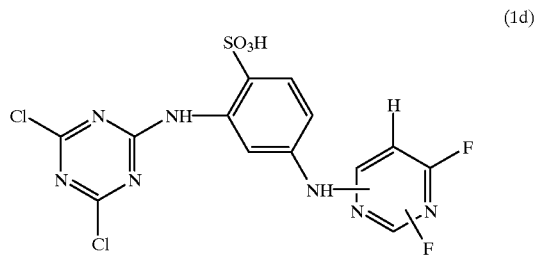

(1d)

is condensed with 100 parts of 2,9-diamino-6,13-dichlorotriphenodioxazinedisulphonic acid at 60–70° and pH 5–6. This pH is maintained during the reaction by adding further lithium hydroxide. Dye 1c is isolated by salting out with sodium chloride, filtered and dried at 50° under reduced pressure.

EXAMPLE 2

140 parts of the triphenodioxazine compound of the formula 1a used in Example 1 are provided in 1800 parts of water. A pH of 5–6 is set by means of lithium hydroxide. 20 parts of 1,3-diaminobenzene are added and the mixture is heated to 60–70° while a pH of 5–6 is held by addition of lithium hydroxide. The reaction ends after about four hours. The reaction mixture is then allowed to cool down to room temperature and the resulting compound of the formula 2a

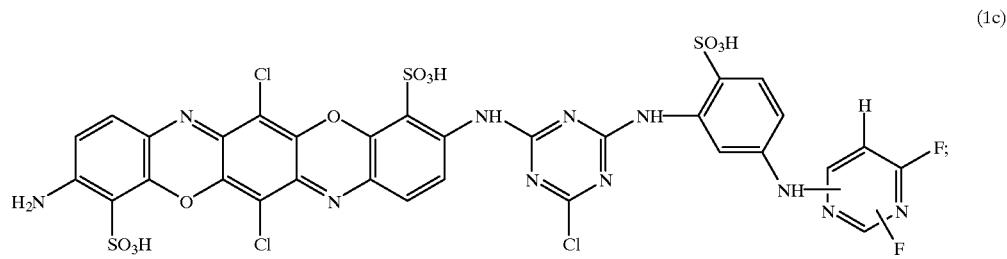

(1c)

It dyes cotton with a high yield of fixation in deep blue shades having good wet fastness properties.

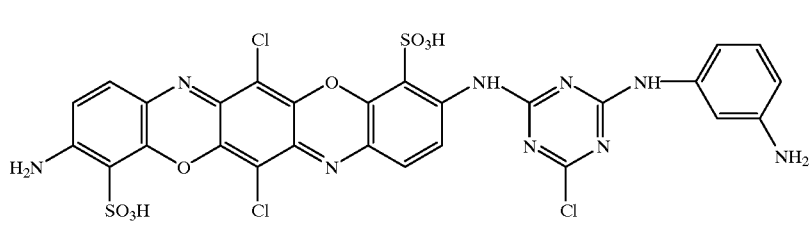

(2a)

is reacted with 24 parts of 2,4,6-trifluoropyrimidine at 0–5°. The condensation reaction is carried out at pH 5–6 using appropriate additions of lithium hydroxide. After the reaction has ended, the dye is salted out with sodium chloride, filtered off and dried at 50° under reduced pressure. The resulting dye in the form of the free acid has the formula 2b.

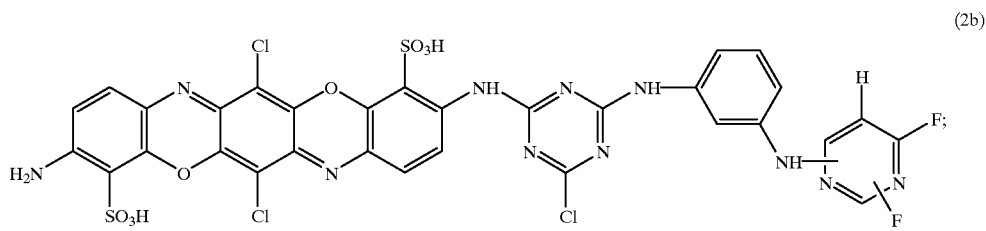

(2b)

It dyes cotton in deep blue shades with a high yield of fixation, the dyeings showing good wet fastness properties.

EXAMPLE 3

The deep blue reaction solution resultiant from Example 2, which comprises the dye of the formula 2b, is further reacted with 34 parts of 5-chloro-2,4,6-trifluoropyrimidine. This condensation reaction is carried out at 15–20° while the pH of the solution is held at 7–8 with lithium hydroxide. After the reaction has ended, the dye is salted out with sodium chloride, filtered off and dried at 50° under reduced pressure. The resulting dye in the form of the free acid has the formula 3

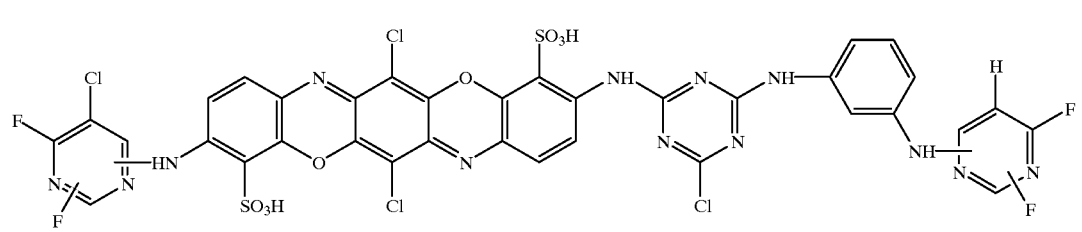

(3)

It dyes cotton in reddish-blue shades with high yields of fixation. These dyeings show good wet fastness properties.

EXAMPLES 4–94

The method described in Examples 1 to 3 can be used for preparing further triphenodioxazine compounds according to the invention. They have the following formula A

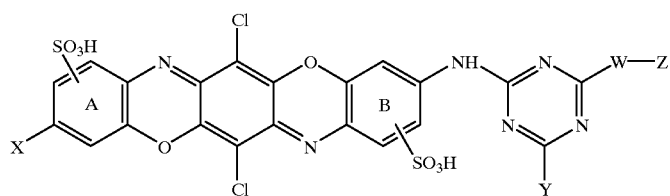

(A)

for which the variables are recited in the table which follows. The sulpho group in the rings A and B is disposed ortho to the radical X or to the triazinylamino radical (both positions are possible).

The W column recites the diamines used for introducing the bridge member W into compounds of the formula A. The linking to the triazine ring and the radical Z is in each case effected via the amino group. Each diamine can be attached to the triazine ring with either end, although in the case of asymmetric diamines the adopted synthesis route plays a part.

Furthermore, the reactive radical Z is represented by the following symbols $Z_1$ to $Z_4$ in the meaning of:

$Z_1$ is

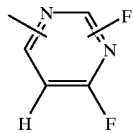

$Z_3$ is

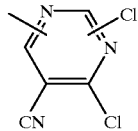

$Z_2$ is

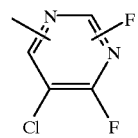

$Z_4$ is

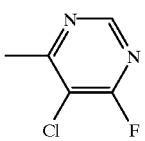

TABLE

Compounds of the formula A

| Ex. No. | W (derived from a diamine of the formula) | Z | X | Y |
|---|---|---|---|---|
| 4 | ![H2N-C6H3(SO3H)-NH2] | $Z_2$ | —$NH_2$ | Cl |
| 5 | " | $Z_1$ | " | F |
| 6 | " | $Z_3$ | —$NHCH_3$ | Cl |
| 7 | " | $Z_2$ | —NH-$Z_2$ | Cl |
| 8 | " | $Z_1$ | —NH-$Z_3$ | Cl |
| 9 | " | $Z_1$ | —$NHC_2H_5$ | Cl |
| 10 | " | $Z_1$ | —NH-$Z_2$ | Cl |
| 11 | " | $Z_4$ | $NH_2$ | Cl |
| 12 | " | $Z_4$ | " | F |
| 13 | ![H2N-C6H4-NH2] | $Z_1$ | —$NH_2$ | F |

TABLE-continued

Compounds of the formula A

| Ex. No. | W (derived from a diamine of the formula) | Z | X | Y |
|---|---|---|---|---|
| 14 | " | $Z_2$ | —NH-$Z_2$ | Cl |
| 15 | " | $Z_3$ | —NHCH$_2$CH$_2$SO$_3$H | Cl |
| 16 | " | $Z_1$ | —NHCH$_2$CH$_2$OH | Cl |
| 17 | " | $Z_4$ | —NHCH$_3$ | Cl |
| 18 | " | $Z_1$ | " | F |
| 19 | " | $Z_3$ | —NH$_2$ | Cl |
| 20 | ![4-methoxy-substituted benzene with H$_2$N, NH$_2$, OCH$_3$, OCH$_3$] | $Z_1$ | " | Cl |
| 21 | " | $Z_3$ | " | Cl |
| 22 | " | $Z_2$ | —NHCH$_3$ | F |
| 23 | ![benzene with H$_2$N, SO$_3$H, NH$_2$] | $Z_1$ | —NH$_2$ | Cl |
| 24 | " | $Z_2$ | " | F |
| 25 | " | $Z_3$ | —NHCH$_3$ | Cl |
| 26 | ![benzene with H$_2$N, SO$_3$H, SO$_3$H, NH$_2$] | $Z_1$ | —NH$_2$ | Cl |
| 27 | " | $Z_2$ | " | Cl |
| 28 | " | $Z_3$ | —NHC$_2$H$_5$ | Cl |
| 29 | " | $Z_1$ | —NHCH$_3$ | F |
| 30 | ![benzene with H$_2$N, OCH$_3$, NH$_2$] | $Z_1$ | —NH$_2$ | Cl |
| 31 | " | $Z_1$ | —NH-$Z_2$ | Cl |
| 32 | " | $Z_3$ | —NH$_2$ | F |
| 33 | " | $Z_4$ | —NHCH$_3$ | Cl |
| 34 | ![benzene with H$_2$N, SO$_3$H, CH$_3$, NH$_2$] | $Z_1$ | —NH$_2$ | Cl |
| 35 | " | $Z_2$ | " | F |

TABLE-continued

Compounds of the formula A

| Ex. No. | W (derived from a diamine of the formula) | Z | X | Y |
|---|---|---|---|---|
| 36 | 2,4-diamino-3-methylbenzenesulfonic acid (H₂N, NH₂, CH₃, SO₃H on benzene) | $Z_1$ | " | F |
| 37 | " | $Z_1$ | —NH-$Z_2$ | Cl |
| 38 | " | $Z_1$ | —NH$_2$ | Cl |
| 39 | 2,5-diaminobenzoic acid (H₂N, NH₂, COOH on benzene) | $Z_1$ | " | Cl |
| 40 | " | $Z_1$ | —NH-$Z_2$ | Cl |
| 41 | " | $Z_2$ | " | F |
| 42 | " | $Z_3$ | —NHCH$_2$CH$_2$OH | Cl |
| 43 | 2,4-diaminobenzoic acid (H₂N, NH₂, COOH on benzene) | $Z_1$ | —NH$_2$ | Cl |
| 44 | 2,4-diaminobenzoic acid (H₂N, NH₂, COOH on benzene) | $Z_1$ | —NHC$_2$H$_5$ | Cl |
| 45 | " | $Z_1$ | —NH$_2$ | F |
| 46 | " | $Z_2$ | " | Cl |
| 47 | 3,5-diaminobenzoic acid (H₂N, NH₂, COOH on benzene) | $Z_1$ | " | Cl |
| 48 | " | $Z_3$ | —NHCH$_3$ | Cl |
| 49 | " | $Z_1$ | —NH-$Z_3$ | Cl |
| 50 | " | $Z_2$ | —NH$_2$ | Cl |
| 51 | " | $Z_1$ | —NHCH$_3$ | F |
| 52 | " | $Z_2$ | —NHC$_2$H$_5$ | Cl |
| 53 | 4-chloro-1,3-diaminobenzene (H₂N, NH₂, Cl on benzene) | $Z_1$ | —NH$_2$ | Cl |
| 54 | " | $Z_2$ | " | F |
| 55 | " | $Z_4$ | " | Cl |
| 56 | " | $Z_3$ | —NHCH$_2$CH$_2$OH | Cl |

TABLE-continued
Compounds of the formula A
| Ex. No. | W (derived from a diamine of the formula) | Z | X | Y |
|---|---|---|---|---|
| 57 | 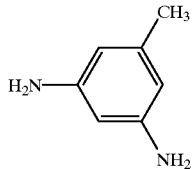 | $Z_1$ | —$NH_2$ | Cl |
| 58 | " | $Z_2$ | —$NHCH_3$ | Cl |
| 59 | " | $Z_3$ | —$NH_2$ | Cl |
| 60 | 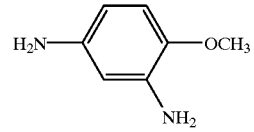 | $Z_1$ | —$NH_2$ | Cl |
| 61 | " | $Z_1$ | —NH-$Z_2$ | Cl |
| 62 | " | $Z_1$ | —$NHCH_3$ | Cl |
| 63 | " | $Z_3$ | —$NH_2$ | F |
| 64 | " | $Z_4$ | " | Cl |
| 65 | 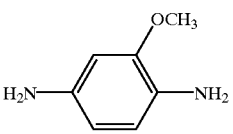 | $Z_1$ | —$NHCH_2CH_2OH$ | Cl |
| 66 | " | $Z_1$ | " | F |
| 67 | " | $Z_2$ | —$NH_2$ | Cl |
| 68 | " | $Z_3$ | " | F |
| 69 | 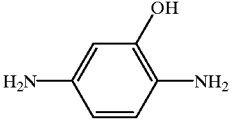 | $Z_1$ | " | Cl |
| 70 | " | $Z_2$ | " | Cl |
| 71 | " | $Z_1$ | —NH-$Z_3$ | Cl |
| 72 | 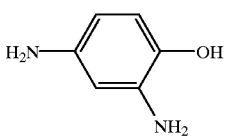 | $Z_1$ | —$NH_2$ | Cl |
| 73 | " | $Z_3$ | " | Cl |
| 74 |  | $Z_1$ | —NH-$Z_2$ | Cl |
| 75 | 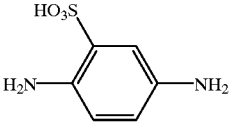 | $Z_1$ | —$NH_2$ | Cl |
| 76 | " | $Z_1$ | " | F |
| 77 | " | $Z_2$ | —NH-$Z_2$ | Cl |
| 78 | " | $Z_3$ | —$NH_2$ | Cl |

TABLE-continued

Compounds of the formula A

| Ex. No. | W (derived from a diamine of the formula) | Z | X | Y |
|---|---|---|---|---|
| 79 | H₂N–C₆H₃(SO₃H)–C₆H₃(SO₃H)–NH₂ (4,4'-diamino-2,2'-biphenyldisulfonic acid) | $Z_1$ | —$NH_2$ | Cl |
| 80 | " | $Z_2$ | —$NHCH_3$ | Cl |
| 81 | " | $Z_1$ | —$NH$-$Z_2$ | Cl |
| 82 | H₂N–C₆H₃(OCH₃)–C₆H₃(OCH₃)–NH₂ (4,4'-diamino-3,3'-dimethoxybiphenyl) | $Z_1$ | —$NH_2$ | F |
| 83 | " | $Z_2$ | " | Cl |
| 84 | " | $Z_4$ | —$NHCH_3$ | Cl |
| 85 | H₂N–C₆H₂(SO₃H)(CH₃)–C₆H₂(CH₃)(SO₃H)–NH₂ | $Z_2$ | —$NH$-$Z_2$ | Cl |
| 86 | " | $Z_1$ | —$NH_2$ | F |
| 87 | " | $Z_3$ | " | Cl |
| 88 | H₂N–C₆H₃(SO₃H)–CH=CH–C₆H₃(SO₃H)–NH₂ | $Z_1$ | " | Cl |
| 89 | " | $Z_1$ | —$NH$-$Z_2$ | Cl |
| 90 | H₂N–C₆H₃(SO₃H)–CH=CH–C₆H₃(SO₃H)–NH₂ | $Z_2$ | —$NH_2$ | Cl |
| 91 | " | $Z_1$ | " | F |
| 92 | " | $Z_3$ | —$NHCH_3$ | Cl |
| 93 | " | $Z_3$ | —$NH_2$ | Cl |
| 94 | " | $Z_2$ | " | F |

The dyes of Examples 4–94 dye cotton in reddish blue to deep blue shades. The dyeings obtained have very good fastness properties.

The above-described methods afford the dyes of Examples 1 to 94 as sodium salts. Depending on the reaction and isolation conditions chosen or else by subsequent measures, they can be prepared in a conventional manner in the form of the free acid or in some other salt form or else mixed salt form and in that case contain for example one or more of the cations further recited in the description.

The dyes of the above-described examples (as a free acid or in any salt form), if they carry one of the reactive radicals $Z_1$ to $Z_3$, contain the compound in which the unfixed fluorine or chlorine substituent is in the 2-position of the pyrimidine ring and the corresponding compound in which this substituent is in the 6-position.

In addition, the dyes of Examples 1–94 can also be mixtures of positional isomers as regards the substitution in the triphenodioxazine ring skeleton.

In general, it is preferred to use the as-synthesized isomer mixture as such; separation into the individual isomers is thus not necessary, but can, if desired, be effected in a conventional manner.

Below the absorption maximum $\lambda_{max}$ is reported in nm for the dye examples. The measurements were carried out in an 8:2 mixture of dimethylformamide and water.

| Ex. No. | $\lambda_{max}$ |
|---|---|
| 1 | 592 |
| 2 | 603 |
| 3 | 571 |
| 4 | 593 |
| 5 | 594 |
| 6 | 592 |
| 7 | 573 |
| 8 | 570 |
| 9 | 592 |
| 10 | 572 |
| 11 | 593 |
| 12 | 593 |
| 13 | 601 |
| 14 | 571 |
| 15 | 603 |
| 16 | 604 |
| 17 | 601 |
| 18 | 601 |
| 19 | 602 |
| 20 | 602 |
| 21 | 602 |
| 22 | 603 |
| 23 | 596 |
| 24 | 596 |
| 25 | 595 |
| 26 | 591 |
| 27 | 592 |
| 28 | 593 |
| 29 | 593 |
| 30 | 598 |
| 31 | 573 |
| 32 | 598 |
| 33 | 598 |
| 34 | 593 |
| 35 | 593 |
| 36 | 592 |
| 37 | 574 |
| 38 | 593 |
| 39 | 596 |
| 40 | 573 |
| 41 | 572 |
| 42 | 596 |
| 43 | 597 |
| 44 | 595 |
| 45 | 595 |
| 46 | 596 |
| 47 | 598 |
| 48 | 599 |
| 49 | 572 |
| 50 | 599 |
| 51 | 599 |
| 52 | 598 |
| 53 | 604 |
| 54 | 604 |
| 55 | 602 |
| 56 | 603 |
| 57 | 601 |
| 58 | 603 |
| 59 | 601 |
| 60 | 604 |
| 61 | 575 |
| 62 | 603 |
| 63 | 604 |
| 64 | 604 |
| 65 | 606 |
| 66 | 605 |
| 67 | 604 |
| 68 | 605 |
| 69 | 603 |
| 70 | 603 |
| 71 | 574 |
| 72 | 600 |
| 73 | 602 |
| 74 | 574 |
| 75 | 576 |
| 76 | 597 |
| 77 | 577 |
| 78 | 590 |
| 79 | 602 |
| 80 | 604 |
| 81 | 573 |
| 82 | 606 |
| 83 | 600 |
| 84 | 603 |
| 85 | 598 |
| 86 | 601 |
| 87 | 602 |
| 88 | 604 |
| 89 | 587 |
| 90 | 599 |
| 91 | 604 |
| 92 | 595 |
| 93 | 601 |
| 94 | 602 |

APPLICATION EXAMPLE A 10 parts of bleached cotton are placed in a dyebath at 50° comprising 0.3 part of the dye of Example 1 and 8 parts of calcined Glauber salt in 100 parts of demineralized water. After 30 minutes at 50° 0.4 part of calcined sodium carbonate is added while the temperature is held at 50°. The temperature is then raised to 60° and the dyeing is continued at 60° for one hour. Thereafter the dyed material is rinsed in running cold water for 3 minutes and then in running hot water for a further 3 minutes. The dyeing is washed at the boil for 15 minutes in 500 parts of demineralized water in the presence of 0.25 part of Marseilles soap. After rinsing for 3 minutes in running hot water, the dyeing is centrifuged and dried at about 70° in a drying cabinet. The result obtained is a deep blue cotton dyeing having very good fastness properties.

APPLICATION EXAMPLE B 10 parts of bleached cotton material are placed in a dyebath comprising 5 parts of calcined Glauber salt in 100 parts of demineralized water. The bath is heated to 50° over 10 minutes, and then 0.5 part of the dye of Example 1 is added. After a further 30 minutes at 50° 1 part of calcined sodium carbonate is added, the temperature is then raised to 60°, and dyeing is continued at 60° for a further 45 minutes.

The dyed material is rinsed with running cold water and then with hot water and washed at the boil as described for method A. Rinsing and drying leaves a deep blue cotton dyeing having very good fastness properties.

APPLICATION EXAMPLE C 10 parts of bleached cotton at 50° are placed in a dyebath comprising 0.3 part of the dye of Example 1 and 1.5 parts of calcined Glauber salt in 100 parts of demineralized water. After 30 minutes at 50° 0.4 part of calcined sodium carbonate is added in portions while the temperature is held at 50°. The temperature is then raised to 60° and the dyeing is continued at 60° for one hour. Thereafter the dyed material is rinsed in running cold water for 3 minutes and then in running hot water for a further 3 minutes. The dyeing is washed at the boil for 20 minutes in 500 parts of demineralized water. After rinsing for 3 minutes in running hot water, the dyeing is centrifuged and dried at about 70° in a drying cabinet. The result obtained is a deep blue cotton dyeing having very good fastness properties.

APPLICATION EXAMPLE D 10 parts of bleached cotton are placed in a dyebath consisting of 1 part of calcined Glauber's salt and 100 parts of demineralised water. The dyebath is heated to 50° C. over a period of 10 minutes before adding 0.3 part of a dyestuff mixture consisting of equal parts of the dyestuff of Example 1, the dyestuff of formula (V) and of formula (VI). 1.0 part of calcined sodium carbonate is added to the bath at 50° C. over a period of 30 minutes before increasing the bath temperature to 60° C. and dyeing at this temperature for a further 45 minutes. The dyed cotton is washed for 3 minutes each in cold running water and then hot running water before boil washing in conformity with the methodology of Application Example A. After washing, the dyed cotton is dried at 70° C. to give a brown dyeing. After the addition of both the Glauber's salt and the sodium carbonate the dyestuff mixture exhibits the same shade throughout the duration of the fixing process.

The methodology of the Application Examples can be followed to dye using dyes of any of the other Examples or dye mixtures containing the dyes of said other Examples. The resulting reddish blue to deep blue dyeings or brownish dyeings if a mixture of dyes according to Application Example D is employed have very good fastness properties.

We claim:

1. A dyestuff composition comprising (A) a compound according to formula (I)

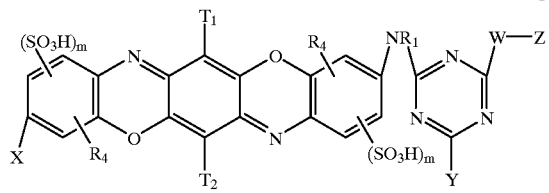

its salts or mixtures thereof,
wherein
$T_1$ and $T_2$ are independently of each other selected from hydrogen, chlorine, bromine, $C_{1-4}$ alkyl, $C_{1-4}$ alkoxy and phenoxy, X is selected from $-NR_2R_3$ and $-NR_1-Z$, each $R_1$ is independently of the other selected from hydrogen, $C_{1-4}$ alkyl, and substituted $C_{1-4}$ alkyl, $R_2$ and $R_3$ are independently of each other selected from hydrogen, $C_{1-4}$ alkyl, substituted $C_{1-4}$ alkyl and cyclohexyl, or $-NR_2R_3$ is a group selected from a 5- or 6-membered heterocyclic ring, a 5- or 6-membered heterocyclic ring having one or two additional hetero atoms selected from oxygen, nitrogen and sulphur atoms and a 5- or 6-membered heterocyclic ring having one or two additional hetero atoms selected from oxygen, nitrogen and sulphur atoms which is further substituted with a group selected from amino, sulpho, hydroxyl, alkyl, alkoxy, fluoro, chloro and bromo, $R_4$ is selected from hydrogen, halogen, $C_{1-4}$ alkyl, $C_{1-4}$ alkoxy and carboxyl, W is selected from an aliphatic, araliphatic, aromatic- and cycloaliphatic diamino bridge member, Y is selected from fluorine, chlorine and $C_{1-4}$ alkoxy, each Z is independently of the other a heterocyclic fibre-reactive radical containing at least one labile fluorine or chlorine atom, and each m is independently of the other 1 or 2; (B) a compound according to the formula (V)

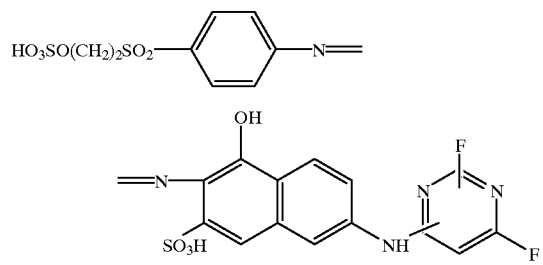

and (C) a compound according to the formula (VI)

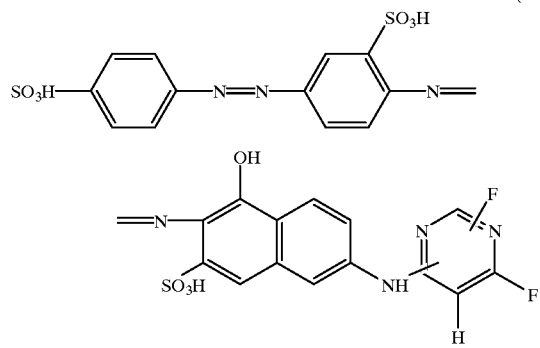

their salts or mixtures thereof.

* * * * *